United States Patent
Yu

(10) Patent No.: US 9,452,018 B2
(45) Date of Patent: Sep. 27, 2016

(54) ROTATIONAL SUPPORT FOR AN ELONGATE MEMBER

(71) Applicant: Hansen Medical, Inc., Mountain View, CA (US)

(72) Inventor: Alan Yu, Union City, CA (US)

(73) Assignee: HANSEN MEDICAL, INC., Mountain View, CA (US)

(*) Notice: Subject to any disclaimer, the term of this patent is extended or adjusted under 35 U.S.C. 154(b) by 811 days.

(21) Appl. No.: 13/833,531

(22) Filed: Mar. 15, 2013

(65) Prior Publication Data
US 2014/0276935 A1    Sep. 18, 2014

(51) Int. Cl.
*A61B 19/00* (2006.01)
*A61M 25/09* (2006.01)

(52) U.S. Cl.
CPC ........... *A61B 19/2203* (2013.01); *A61B 34/30* (2016.02); *A61B 34/37* (2016.02); *A61B 2034/301* (2016.02); *A61M 25/09041* (2013.01)

(58) Field of Classification Search
CPC .. A61B 1/018; A61B 17/3421; A61B 19/22; A61B 7/29; A61B 17/3417; A61B 19/30; A61B 2017/003; A61M 2025/0008
USPC .......................................... 600/433, 434, 585
See application file for complete search history.

(56) References Cited

U.S. PATENT DOCUMENTS

| | | | |
|---|---|---|---|
| 5,398,691 A | 3/1995 | Martin et al. | |
| 5,408,409 A | 4/1995 | Glassman et al. | |
| 5,524,180 A | 6/1996 | Wang et al. | |
| 5,631,973 A | 5/1997 | Green | |
| 5,713,946 A | 2/1998 | Ben-Haim | |
| 5,749,362 A | 5/1998 | Funda et al. | |
| 5,859,934 A | 1/1999 | Green | |
| 5,876,325 A | 3/1999 | Mizuno et al. | |
| 5,951,475 A | 9/1999 | Gueziec et al. | |
| 6,226,543 B1 | 5/2001 | Gilboa et al. | |
| 6,259,806 B1 | 7/2001 | Green | |
| 6,272,371 B1 | 8/2001 | Shlomo | |
| 6,424,885 B1 | 7/2002 | Niemeyer et al. | |
| 6,726,675 B1 | 4/2004 | Beyar | |
| 7,155,315 B2 | 12/2006 | Niemeyer et al. | |
| 2006/0025676 A1 | 2/2006 | Viswanathan et al. | |
| 2006/0161045 A1* | 7/2006 | Merril | A61B 1/018 600/117 |

FOREIGN PATENT DOCUMENTS

WO   03086190 A1   10/2003

* cited by examiner

*Primary Examiner* — Max Hindenburg
*Assistant Examiner* — Jonathan M Foreman
(74) *Attorney, Agent, or Firm* — Dorsey & Whitney LLP; Scott M. Smith

(57) ABSTRACT

Various exemplary drive apparatuses and associated methods are disclosed for driving an elongated member, e.g., a guidewire or catheter. An exemplary drive apparatus for driving an elongated member may include a rotational component configured to apply a torque to the elongated member, where the rotational component is positioned a first distance away from an insertion site along the elongated member. The drive apparatus may further include a rotational support configured to apply an assistance torque to the elongated member. The rotational support may be positioned a second distance from the rotational component along the elongated member that is larger than the first distance.

18 Claims, 3 Drawing Sheets

US 9,452,018 B2

ROTATIONAL SUPPORT FOR AN ELONGATE MEMBER

BACKGROUND

Robotic interventional systems and devices are well suited for performing minimally invasive medical procedures as opposed to conventional techniques wherein the patient's body cavity is open to permit the surgeon's hands access to internal organs. However, advances in technology have led to significant changes in the field of medical surgery such that less invasive surgical procedures, in particular, minimally invasive surgery (MIS), are increasingly popular.

A MIS is generally defined as a procedure that is performed by entering the body through the skin, a body cavity, or an anatomical opening utilizing small incisions rather than large, open incisions in the body. With MIS, it is possible to achieve less operative trauma for the patient, reduced hospitalization time, less pain and scarring, reduced incidence of complications related to surgical trauma, lower costs, and a speedier recovery.

Special medical equipment may be used to perform MIS procedures. Typically, a surgeon inserts small tubes or ports into a patient and uses endoscopes or laparoscopes having a fiber optic camera, light source, or miniaturized surgical instruments.

MIS apparatus and techniques have advanced to the point where an insertion and rolling motion of components of an elongated component such as a catheter instrument, e.g., a catheter sheath and associated guidewire, are generally controllable by selectively operating rollers or other mechanisms for generally gripping the component. Due to the length and complexity of catheter instruments and components thereof, rotation of the catheter may be generally difficult to control.

Accordingly, there is a need in the art for systems and methods for inserting and rolling catheter components that address or solve the above problems.

SUMMARY

An exemplary method of driving an elongated member, e.g., a guidewire or catheter, merely as examples, may include applying a first torque to the elongated member with a rotational component that is positioned a first distance away from an insertion site along the elongated member. The exemplary method may further include applying an assistance torque to the elongated member with a rotational support positioned a second distance away from an insertion site along the elongated member, where the second distance is larger than the first distance.

An exemplary drive apparatus for driving an elongated member may include a rotational component configured to apply a torque to the elongated member, where the rotational component is positioned a first distance away from an insertion site along the elongated member. The drive apparatus may further include a rotational support configured to apply an assistance torque to the elongated member. The rotational support may be positioned a second distance from the rotational component along the elongated member that is larger than the first distance.

BRIEF DESCRIPTION OF THE DRAWINGS

While the claims are not limited to the illustrated embodiments, an appreciation of various aspects is best gained through a discussion of various examples thereof. Referring now to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limiting or restricting to the precise form and configuration shown in the drawings and disclosed in the following detailed description. Exemplary embodiments of the present invention are described in detail by referring to the drawings as follows.

DETAILED DESCRIPTION

Figure 1:
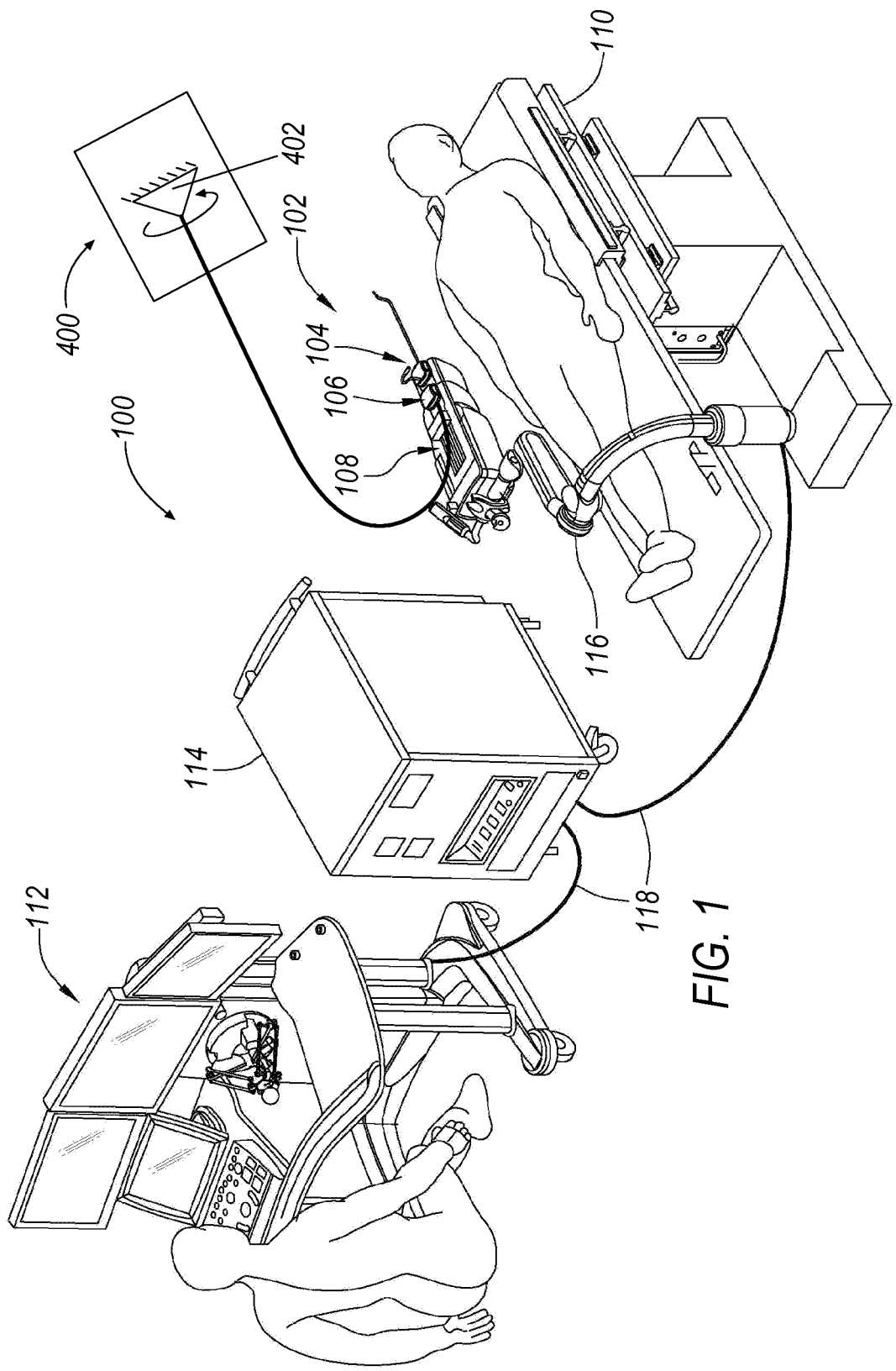
FIG. 1 is an illustration of a robotically controlled surgical system, according to one exemplary illustration.

Referring now to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limit or restrict the invention to the precise form and configuration shown in the drawings and disclosed in the following detailed description.

Referring to FIG. 1, a robotically controlled surgical system 100 is illustrated in which an apparatus, a system, and/or method may be implemented according to various exemplary illustrations. System 100 may include a robotic catheter assembly 102 having a robotic or first or outer steerable complement, otherwise referred to as a sheath instrument 104 (generally referred to as "sheath" or "sheath instrument") and/or a second or inner steerable component, otherwise referred to as a robotic catheter or guide or catheter instrument 106 (generally referred to as "catheter" or "catheter instrument"). Catheter assembly 102 is controllable using a robotic instrument driver 108 (generally referred to as "instrument driver").

Moreover, as described further below in regard to FIGS. 2 and 3, a rotational support 400 may be provided which is configured to provide an assistance torque to an elongate member that is part of the catheter assembly 102. For example, a rotational support 400 may be configured to provide an assistance torque to a guidewire inserted coaxially into the catheter 102 assembly, e.g., within a catheter sheath. The rotational support 400 may be used to support an elongated member such as the guidewire rotationally, to allow a greater degree of control over the rotation of the elongate member.

During use, a patient is positioned on an operating table or surgical bed 110 (generally referred to as "operating table") to which robotic instrument driver 108 may be coupled or mounted. In the illustrated example, system 100 includes an operator workstation 112, an electronics rack 114 and associated bedside electronics box (not shown), a setup joint mounting brace 116, and instrument driver 108. A surgeon is seated at operator workstation 112 and can monitor the surgical procedure, patient vitals, and control one or more catheter devices. Operator workstation 112 may include a computer monitor to display a three dimensional object, such as a catheter instrument or component thereof, e.g., a guidewire, catheter sheath. Moreover, a catheter instrument may be displayed within or relative to a three dimensional space, such as a body cavity or organ, e.g., a chamber of a patient's heart. In one example, an operator uses a computer mouse to move a control point around the display to control the position of catheter instrument.

System components may be coupled together via a plurality of cables or other suitable connectors 118 to provide for data communication, or one or more components may be equipped with wireless communication components to reduce or eliminate cables 118. Communication between components may also be implemented over a network or over the internet. In this manner, a surgeon or other operator may control a surgical instrument while being located away from or remotely from radiation sources, thereby decreasing radiation exposure. Because of the option for wireless or networked operation, the surgeon may even be located remotely from the patient in a different room or building.

Figure 2:
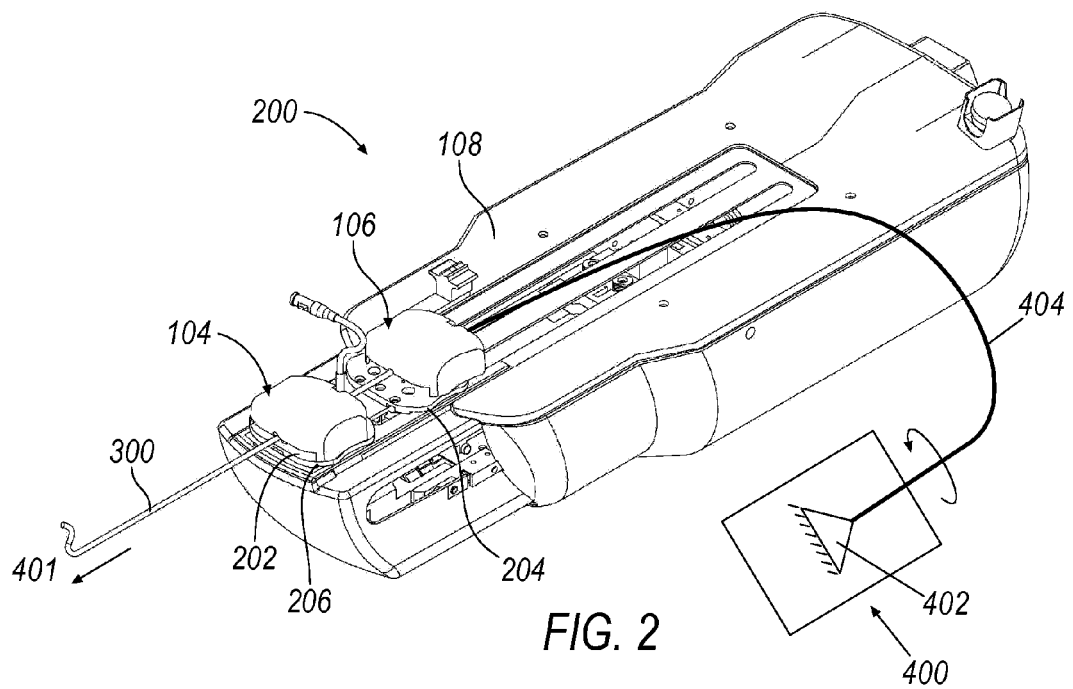
FIG. 2 is an illustration of an exemplary catheter assembly of the surgical system of FIG. 1.

Referring now to FIG. 2, an exemplary drive assembly 200 is shown in further detail, including sheath instrument 104 and the associated guide or catheter instrument 106 mounted to mounting plates 202, 204 on a top portion of instrument driver 108. During use, catheter instrument 106 is inserted within a central lumen of sheath instrument 104 such that instruments 104, 106 are arranged in a coaxial manner. Although instruments 104, 106 are arranged coaxially, movement of each instrument 104, 106 can be controlled and manipulated independently. For this purpose, motors within instrument driver 108 are controlled such that carriages coupled to each of the instruments 104, 160 may allow the instruments 104, 106 to be driven forwards and backwards along the driver 108, e.g., with mounting plates securing the instruments to the driver 108 on bearings. As a result, a catheter 300 coupled to guide catheter instrument 106 and sheath instrument 104 can be controllably manipulated while inserted into the patient, as will be further illustrated. Additional instrument driver 108 motors (not shown in FIG. 2) may be activated to control bending of the catheter as well as the orientation of the distal tips thereof, including tools mounted at the distal tip. Sheath catheter instrument 106 is configured to move forward and backward for effecting an axial motion of the catheter, e.g., to insert and withdraw the catheter from a patient, respectively. For example, the catheter 300 is configured to be inserted and removed from the patient's body at an insertion site 401.

At least one of the instruments 104, 106 may apply a torque to an elongated member included in the catheter 300. For example, a guidewire 404 may be inserted into the instruments 104, 106 for guiding the catheter 300. In one exemplary illustration, the instrument 106 applies a torque to the guidewire 404, e.g., to impart a rotational motion for guidance of the catheter. The rotational support 400, which is positioned further away from the insertion site 401 than the instrument 106, may apply an assistance torque to the guidewire 404, and end of which is attached to the rotational support 400 at a fixture 402. In some exemplary approaches described further below, the assistance torque may be a larger amount than that applied by the instrument 106. In another example, the assistance torque is applied as a "coarse" adjustment relative to torque being applied by the instrument 106, wherein torque is applied to the guidewire 404 in relatively large amounts via the rotational support 400. By contrast, torque may be more finely adjusted by the instrument 106. In this manner, the application of torque using the rotational support 400 and the instrument 106 is similar to a physician using two hands to rotate the wire, where the hand closest to the operating/insertion site makes fine torque adjustments, perhaps with only the fingertips, while the rearward hand makes relatively larger "gross" torque adjustments with the hand grasping the wire. Moreover, the rotational support 400 may have a relatively tighter grip on the rearward end of the guidewire, as will be described further below.

Figure 3:
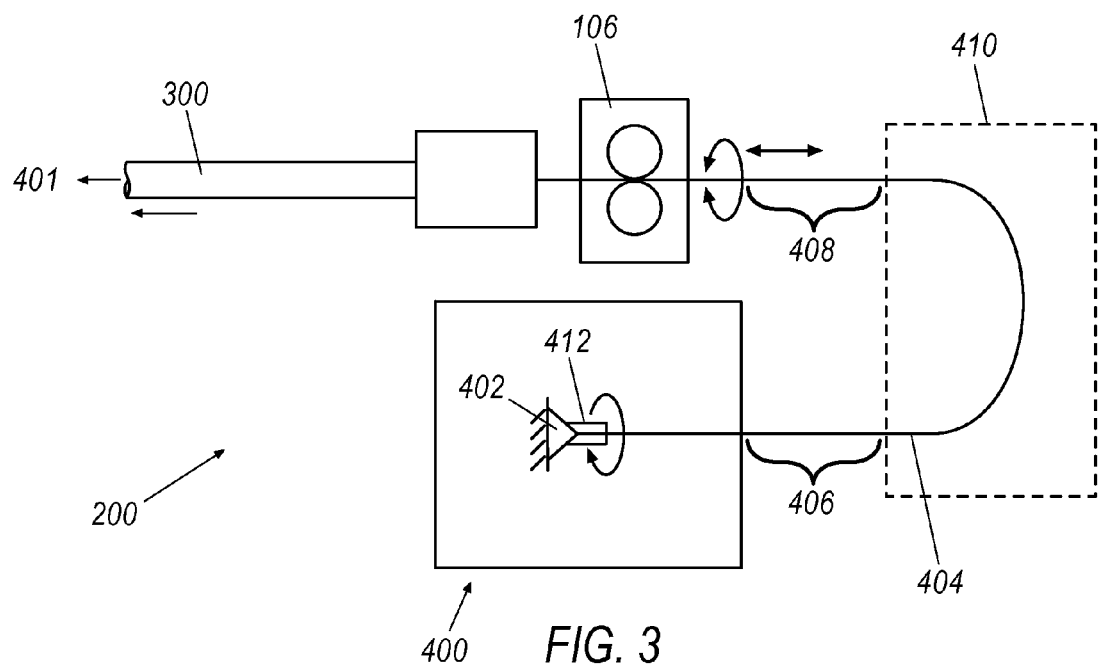
FIG. 3 is a schematic view of the exemplary illustration of an exemplary catheter assembly of the surgical system of FIGS. 1 and 2.

Referring now to FIG. 3, the exemplary drive assembly 200 is illustrated in further detail. The rotational component or instrument 106, as noted above, may be configured to apply a torque to the elongated member, e.g., a guidewire 404, while the rotational support 400 is configured to apply an assistance torque to the elongated member. The guidewire 404 includes a turned portion 406 which is wrapped approximately 180 degrees with respect to another portion 408 that is aligned for insertion into the instrument 106. The turning of the guidewire 404 may generally facilitate insertion of the guidewire 404, i.e., by placing the end 408 of the guidewire 404 relatively close to the instrument 106. Accordingly, during insertion of the guidewire 404 into the instrument 106, the lengths of the turned portion 406 and the aligned portion may decrease as a greater length overall of the guidewire 404 is inserted. As a result of the turning of the wire, e.g., to the 180 degree orientation, the rotational support 400 does not require movement relative to the rotational component 106. Alternatively, if the elongate member were oriented straight, i.e., such that the entire elongate member were aligned along the insertion axis of the instrument 106, the rotational support 400 would be required to mount to a moveable carriage to allow insertion and retraction of the elongate member.

The turning of the guidewire 404 may also facilitate the use of an intermediate support 410 for the guidewire 404 in between the rotational support 400 and the instrument 106. In particular, to the extent there is any different in torque or rotational movement being applied to the guidewire 404 by the rotational support 400 on the one hand and the instrument 106 on the other, an intermediate support 410 may generally prevent the guidewire 404 from twisting. In one exemplary approach, the intermediate support 410 includes two planar members generally sandwiching the guidewire 404 therebetween. Accordingly, the guidewire 404 is generally forced to remain substantially in a single plane. Moreover, the use of two planar members may generally freely permit movement of the guidewire 404 as a result of insertion, i.e., taking up more of the slack in the guidewire. As another example, the guidewire 404 may be placed in a track (not shown). As yet another example, one or more weights (not shown) may be applied or secured to the guidewire 404, e.g., along a length of the guidewire 404 intermediate the rotational support 400 and the instrument 106, to inhibit vertical movement of the guidewire 404, thereby preventing the guidewire 404 from twisting upon itself.

The rotational support 400 may generally anchor or fix the end to an infinitely rotatable support 402. For example, the support 402 may be a collet comprising a sleeve 412 that extends from the end of the elongated member, i.e., the guidewire, along a length of the elongated member. The end of the guidewire 404 may thereby be generally anchored to the rotational support 400. Moreover, the end of the guidewire may be generally gripped or anchored in a far more aggressive manner than generally possible for the instrument 106, as the instrument 106 must generally be configured to apply fine torque adjustments to the guidewire 404. Moreover, the instrument 106 must generally not damage the guidewire 406. By contrast, the end of the guidewire 404 may be anchored or clamped within the rotational support 400 as aggressively as possible to maintain a relatively firm grip on the guidewire. The end of the guidewire 404 is generally permanently fixed to the rotational support 400, and can be clamped aggressively, without any regard for damage to the guidewire 404 that the instrument 106, on the other hand, must generally avoid. Moreover, in one exemplary illustration, the end of the guidewire 404 is grabbed by a disposable component through a sterile drape (not shown in FIG. 3), allowing the rotational support 400 to remain under the sterile drape. Accordingly, reuse of the rotational support 400 for subsequent procedures is generally possible.

In some exemplary approaches, as noted above the rotational support 400 may be configured to adjust the assistance torque in relatively large increments as a "gross" adjustment, while the rotational component, i.e., instrument 106, is configured to apply torque adjustments in smaller increments as a "fine" adjustment. Moreover, the rotational support 400 may include any rotational device that is convenient, e.g., an infinitely rotatable tool such as a geared wheel (not shown) or other mechanism configured to rotate continuously. Accordingly, the rotational support 400 need not be limited to any particular rotational range of motion. Moreover, the use of an infinitely rotatable tool also facilitates the generally permanent clamping of the end of the guidewire 404, since there is no need to release and re-grip the guidewire 404.

In another exemplary illustration, the rotational support 400 may be used to apply a proportionally greater rotational movement or torque to an elongate member, e.g., guidewire 404. In some exemplary approaches, the rotational component, i.e., instrument 106, may generally be used to selectively release the guidewire 404 after the application of a relatively larger amount of rotation and/or torque that is needed in a given procedure. More specifically, the rotational support 400 may be used to "wind up" the guidewire to a magnitude, e.g., a torque, that generally exceeds a torque expected for a given procedure or movement of the elongate member. Subsequently, the instrument 106 may selectively "deploy" the torque present in the length of the elongate member between the instrument 106 and the rotational support 400 to the length of the elongate member in between the instrument 106 and an insertion site, e.g., insertion site 401.

In another example, for each magnitude of rotation applied to the guidewire 404 by the instrument 106, the rotational support 400 may rotate a larger magnitude. In one example, the rotational support 400 turns four times more than the corresponding instrument 106. The particular relationship between the magnitude of the rotation of the rotation support 400 and the instrument 106 will be dependent on the wire length and type. For example, where a larger length of the elongated member, e.g., guidewire 400 is employed, the greater length may allow a larger difference in rotation between the rotational support 400 and the instrument 106. Additionally, where a more delicate elongate member is employed, a comparatively smaller difference in rotation between the rotational support 400 and the instrument 106 may be employed in view of the increased likelihood of damaging the elongate member.

Figure 4:
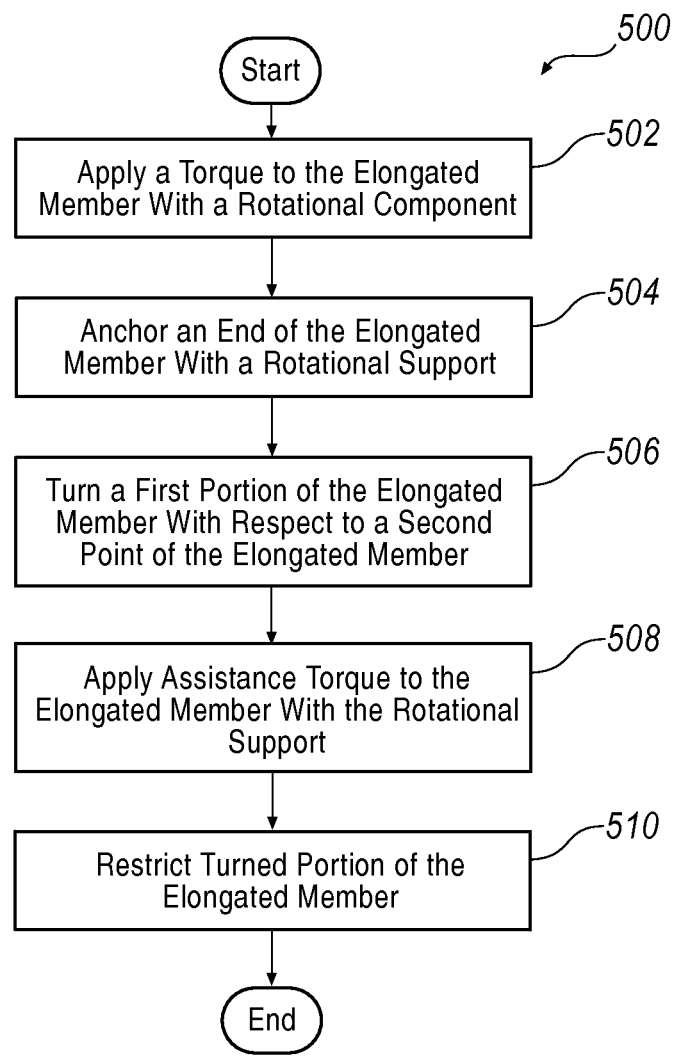
FIG. 4 is process flow diagram for an exemplary method of driving an elongated member.

Referring now to FIG. 4, an exemplary process 400 of driving an elongated member is described. Process 400 may begin at block 402, where a first torque is applied to an elongate member with a rotational component. For example, as described above a first torque may be applied to an elongate member, e.g., guidewire 404, with a rotational component, e.g., instrument 106. The instrument 106 may be positioned a first distance away from an insertion site along the elongated member, such that it is closer to the insertion site than an associated rotational support, e.g., rotational support 400. Process 400 may then proceed to block 404.

At block 404, an end of the elongate member may be anchored with the rotational support. For example, an end of a guidewire 404 may be anchored to a collet 402 or within a sleeve 412 that is configured to secure the end of the guidewire 404. Moreover, the elongate member may be generally deformed within the collet 402 or sleeve 412, as the guidewire 400 need not be handled delicately since the end of the guidewire 404 adjacent the rotational support 400 and an adjacent length is not expected to be used for insertion or to be handled by the instrument 106. As described above, the end of the elongate member, e.g., guidewire 404, may be received within a sleeve 412 that extends along a length of the guidewire 404, thereby facilitating a generally secure grip and allowing application of generally greater torque and/or rotational magnitude than is generally possible with the instrument 106. Process 400 may then proceed to block 406.

At block 406, a first portion of the elongate member may be turned with respect to a second portion of the elongate member. For example, as described above a first portion 406 of a guidewire 404 may be turned such that it is rotated approximately 180 degrees with respect to a second portion 408 that is aligned for insertion into the rotational component, i.e., instrument 106.

Proceeding to block 408, an assistance torque or rotation may be applied to the elongate member with a rotational support, e.g., rotational support 400. The rotational support 400, in some examples as described above, may be positioned generally further away from an insertion site along the elongated member than the rotational component, i.e., the instrument 106. In some exemplary approaches, the assistance torque and/or the rotational movement applied by the rotational support 400 may be greater than the torque and/or rotational movement applied by the rotational component, e.g., instrument 106. In some examples, the rotational component, e.g., instrument 106, may be used to selectively release a portion of the assistance torque being applied by the rotational support 400. More specifically, the rotational support 400 may apply an assistance torque or rotational movement that is relatively larger than expected to be applied by the instrument 106. The instrument 106 may then release a portion of the rotational movement and/or the torque to the portion of the elongate member between the instrument 106 and the insertion site. The assistance torque may function, in some examples, as a coarse torque adjustment with respect to a relatively fine torque adjustment applied by the rotational component, i.e., the instrument 106. For example, the assistance torque may be adjusted or applied in larger increments than the torque applied by the rotational component, i.e., the instrument 106. The rotational support 400 may also have a generally infinite rotational range of motion, e.g., with a generally circular wheel or other continuously rotatable tool, thereby permitting continuous rotational movement to be applied to any degree without requiring releasing or re-gripping the elongate member.

Proceeding to block 410, a turned portion of the elongate member may be restricted, e.g., to inhibit or prevent twisting of the elongate member. For example, as described above a curved portion of the guidewire 404, i.e., extending between a turned portion 406 and an aligned portion 408 of the guidewire may be kept substantially within a predetermined plane. The restriction of the elongate member may be accomplished using corresponding planar members 410 that may be used to generally trap the elongate member, e.g., a guidewire, therebetween, thereby generally preventing movement of the elongate member outside of the plane defined between the two planar members. Moreover, movement of the guidewire 404 within the defined plane may generally be freely allowed, resulting in a minimal restriction on the guidewire 404 that does not overly interfere with the movement of the guidewire 404, e.g., during insertion.

Operator workstation 112, electronics rack 114, drive apparatus 200, and/or rotational support 400 may include a computer or a computer readable storage medium implementing the operation of drive and implementing the various methods and processes described herein, e.g., process 1300. In general, computing systems and/or devices, such as the processor and the user input device, may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., and the Android operating system developed by the Open Handset Alliance.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

The exemplary illustrations are not limited to the previously described examples. Rather, a plurality of variants and modifications are possible, which also make use of the ideas of the exemplary illustrations and therefore fall within the protective scope. Accordingly, it is to be understood that the above description is intended to be illustrative and not restrictive.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "the," "the," etc. should be read to recite one or more of the indicated elements unless a claim recites an explicit limitation to the contrary.

The invention claimed is:

1. A method of driving an elongate member, the method comprising:

applying a first torque to the elongate member with a rotational component positioned a first distance away from an insertion site along the elongate member;

applying an assistance torque to the elongate member with a rotational support positioned a second distance away from the insertion site along the elongate member, the second distance being larger than the first distance;

turning a first portion of the elongate member with respect to a second portion of the elongate member; and restricting the first portion of the elongate member within a predetermined plane.

2. The method of claim 1, wherein the assistance torque is greater than the first torque.

3. The method of claim 1, wherein the assistance torque is a coarse torque adjustment, and the first torque is a fine torque adjustment.

4. The method of claim 1, further comprising adjusting the assistance torque in a first increment, and adjusting the first torque in a second increment smaller than the first increment.

5. The method of claim 1, further comprising anchoring an end of the elongate member with the rotational support.

6. The method of claim 5, wherein anchoring the end of the elongate member includes deforming the elongate member adjacent the end.

7. The method of claim 1, further comprising receiving an end of the elongate member within a sleeve extending from the end of the elongate member along a length of the elongate member.

8. The method of claim 1, wherein the rotational support has an infinite rotational range of motion.

9. The method of claim 1, wherein the first portion of the elongate member is turned 180 degrees from the second portion.

10. The method of claim 1, wherein the elongate member is configured to define variable lengths of the elongate member between the rotational component and the rotational support without relative movement between the rotational component and rotational support.

11. The method of claim 1, wherein driving the elongate member comprises driving a guidewire.

12. The method of claim 1, further comprising selectively releasing a portion of the assistance torque with the rotational component.

13. A method of driving an elongate member, the method comprising:

applying a first torque to the elongate member with a rotational component positioned a first distance away from an insertion site along the elongate member;

turning a first portion of the elongate member with respect to a second portion of the elongate member, wherein the first portion of the elongate member is turned 180 degrees from the second portion of the elongate member;

anchoring an end of the elongate member with the rotational support; and applying an assistance torque to the elongate member with a rotational support positioned a second distance away from an insertion site along the elongate member, the second distance being larger than the first distance.

14. The method of claim 13, wherein a portion of the elongate member is positioned intermediate the rotational component and the rotational support.

15. The method of claim 13, wherein the elongate member is a guidewire.

16. A drive apparatus for driving an elongate member, the drive apparatus comprising:

a rotational component configured to apply a torque to the elongate member, the rotational component positioned a first distance away from an insertion site along the elongate member; and a rotational support configured to apply an assistance torque to the elongate member, the rotational support positioned a second distance from the insertion site along the elongate member, the second distance being larger than the first distance, wherein the rotational support includes a sleeve anchoring an end of the elongate member, the sleeve extending from the end of the elongate member along a length of the elongate member.

17. The drive apparatus of claim 16, further comprising an intermediate support positioned intermediate the rotational component and the rotational support, the intermediate support configured to maintain a turned portion of the elongate member substantially in a single plane.

18. The drive apparatus of claim 16, wherein the rotational support is configured to adjust the assistance torque in a first increment, and the rotational component is configured to adjust the first torque in a second increment smaller than the first increment.

* * * * *